(12) United States Patent
Minter et al.

(10) Patent No.: US 8,598,391 B2
(45) Date of Patent: Dec. 3, 2013

(54) POLYTRIMETHYLENE ETHER GLYCOL OR COPOLYMERS THEREOF HAVING IMPROVED COLOR AND PROCESSES FOR THEIR PREPARATION

(75) Inventors: Aaron Minter, Wilmington, DE (US); Edward R. Murphy, Wilmington, DE (US); Howard C. Ng, Kingston (CA); Rupert Spence, Kingston (CA); Tuyu Xie, Kingston (CA)

(73) Assignee: E I du Pont de Nemours and Company, Wilmington, DE (US)

( * ) Notice: Subject to any disclaimer, the term of this patent is extended or adjusted under 35 U.S.C. 154(b) by 347 days.

(21) Appl. No.: 12/893,078

(22) Filed: Sep. 29, 2010

(65) Prior Publication Data

US 2011/0077433 A1    Mar. 31, 2011

Related U.S. Application Data

(60) Provisional application No. 61/247,141, filed on Sep. 30, 2009.

(51) Int. Cl.
*C07C 41/09* (2006.01)
*C07C 43/13* (2006.01)

(52) U.S. Cl.
CPC ............... *C07C 41/09* (2013.01); *C07C 43/135* (2013.01)
USPC .......................................... 568/619; 568/623

(58) Field of Classification Search
CPC ............................... C07C 41/09; C07C 43/135
USPC .................................................. 568/619, 623
See application file for complete search history.

(56) References Cited

U.S. PATENT DOCUMENTS

| | | |
|---|---|---|
| 4,551,561 A | 11/1985 | Stuhler |
| 5,962,622 A | 10/1999 | Darnell et al. |
| 6,235,948 B1 | 5/2001 | Sunkara et al. |
| 6,270,459 B1 | 8/2001 | Konofagou et al. |
| 6,977,291 B2 | 12/2005 | Sunkara et al. |
| 7,049,390 B2 | 5/2006 | Adelman et al. |
| 7,074,969 B2 | 7/2006 | Sunkara et al. |
| 7,157,607 B1 | 1/2007 | Sunkara et al. |
| 7,161,045 B1 | 1/2007 | Sunkara et al. |
| 7,294,746 B2 | 11/2007 | Sunkara et al. |
| 7,388,115 B2 | 6/2008 | Sunkara et al. |
| 2005/0272911 A1 | 12/2005 | Okoshi et al. |
| 2006/0161027 A1 | 7/2006 | Okoshi et al. |
| 2008/0242831 A1 | 10/2008 | Niu et al. |
| 2009/0118464 A1 | 5/2009 | Harmer et al. |

FOREIGN PATENT DOCUMENTS

| | | | |
|---|---|---|---|
| KR | 1020050012277 A | | 1/2005 |
| KR | 1020070024607 A | | 3/2007 |

OTHER PUBLICATIONS

International Search Report, PCT International Application PCT/US2010/050628, Mailed Jun. 27, 2011.

*Primary Examiner* — Rosalynd Keys

(57) ABSTRACT

Processes for reducing the color of polytrimethylene ether glycol or copolymers thereof are provided. The processes include polycondensing diols in the presence of an acid catalyst and adding base continuously over a period of the polycondensation reaction. The invention also relates to the polytrimethylene ether glycol thereof produced by these processes.

8 Claims, 2 Drawing Sheets

POLYTRIMETHYLENE ETHER GLYCOL OR COPOLYMERS THEREOF HAVING IMPROVED COLOR AND PROCESSES FOR THEIR PREPARATION

FIELD OF THE INVENTION

The invention relates to processes for reducing the color of polymers such as polytrimethylene ether glycol or copolymers thereof by adding base over the course of the polymerization reaction. This invention also relates to the polymers produced by these processes.

BACKGROUND

Polytrimethylene ether glycols can be produced via the acid-catalyzed polycondensation of 1,3-propanediol, optionally in the presence of comonomer diols. Polytrimethylene ether glycol produced in this manner may have quality problems, in particular the color may not be desirable to the industry. The polymer quality depends on the quality of the raw material, and the polymerization process conditions and stability of the polymer are also responsible for discoloration to some extent. Various treatment methods to improve the color of polytrimethylene ether glycols are known, and include purification or pretreatment of 1,3-propanediol prior to the polycondensation reaction. Disclosed in U.S. Pat. No. 6,235,948 is a process for the removal of color-forming impurities from 1,3-propanediol by a preheating with heterogeneous acid catalysts such as perfluorinated ion exchange polymers. Post-polymerization treatment methods with adsorbents such as carbon black, are also disclosed in the art (U.S. Pat. No. 7,294,746).

Both pre- and post-treatment methods add steps to the process for producing commercially acceptable polymer. Attempts have also been made to alter reaction conditions to control product color. For example, U.S. Patent Application Publication No. 2005/272911 discloses methods of controlling color formation by carrying out the dehydration-condensation reaction in the presence of a catalyst composed of an acid and a base, which are included in the beginning of the reaction.

There exists a need for improved and convenient methods to reduce the color of polytrimethylene ether glycol. Ideal methods would allow for polymer to be produced using standard process equipment and reagents and under reaction conditions which yield acceptable reaction times and polymers of desired molecular weights.

SUMMARY OF THE INVENTION

One aspect of the present invention is a process comprising a) polycondensing reactants comprising 1,3-propanediol, poly 1,3-propanediol, or mixtures thereof and optionally a comonomer diol in the presence of an acid catalyst to form a product polymer; and b) adding base during the polycondensing of the reactants.

Another aspect of this invention is polytrimethylene ether glycols produced by this process.

DETAILED DESCRIPTION

Figure 1:
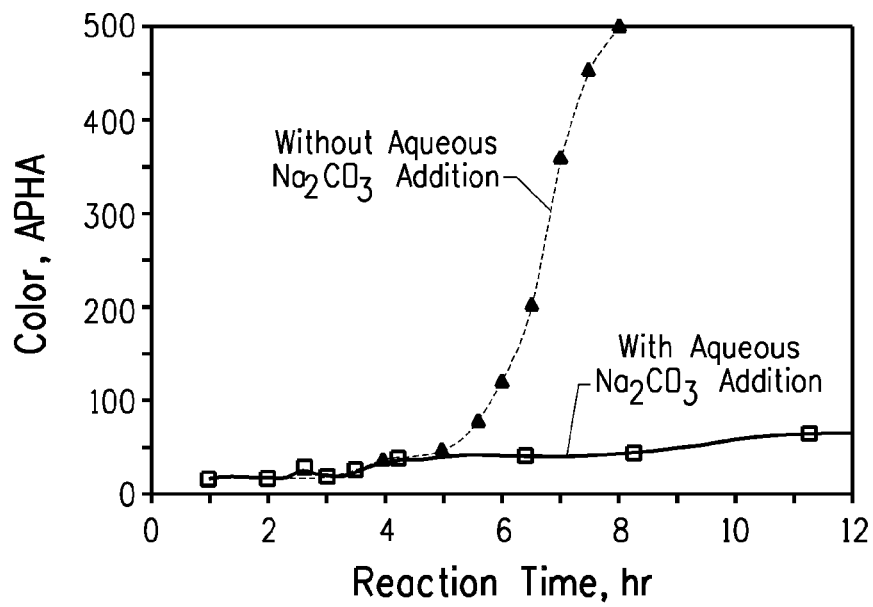
FIG. 1 illustrates the continuous addition of sodium carbonate aqueous solution on polytrimethylene ether glycol color development; 160° C., 3.0 wt % of sulfuric acid.

Provided herein is a process comprising polycondensing reactants comprising 1,3-propanediol, poly 1,3-propanediol, or mixtures thereof and optionally a comonomer diol in the presence of an acid catalyst to form a product polymer. Processes described herein comprise adding base over the course of the polycondensation reaction. In some embodiments, the base is added continuously over a period of the reaction, and, in some embodiments, base is added via multiple aliquots over the course of the reaction. In some embodiments, the product polymer is polytrimethylene ether glycol. In certain embodiments, the comonomer diol is 1,2-ethanediol.

In certain embodiments, the product polymer is polytrimethylene ether glycol and has an APHA color of less than about 250, or less than about 100. In some embodiments, the product polymer has a molecular weight of about 500 to about 5000. Processes disclosed herein can also be used to produce product polymer having a molecular weight of at least about 1000, and in some embodiments about 1400 or greater.

The terms "color" and "color bodies" as used herein refer to the existence of visible color that can be quantified by the use of a spectrocolorimeter in the range of visible light, using wavelengths of approximately 400 to 800 nm, and by comparison with pure water. Color precursors in 1,3-propanediol are not visible in the range of 400 to 800 nm, but contribute color after polymerization.

By "acid catalyst" is meant an acid that promotes the condensation reaction of alcohols to ethers.

By "polycondensation" or "polycondensation reaction" is meant a reaction carried out according to aspects of this invention wherein at least one polycondensation catalyst is used.

By "product polymer" is meant the polymer formed by polycondensation of the reactants comprising 1,3-propanediol or poly-1,3-propanediol or mixtures thereof. For example, the polycondensation of 1,3-propanediol or poly-1,3-propanediol or mixtures thereof in the presence of an acid catalyst leads to the formation of the product polymer polytrimethylene ether glycol. Inclusion of comonomers in the reactants may lead to the formation of product copolymers. When the polycondensation reaction is carried out in the presence of a comonomer diol, at least one copolymer of polytrimethylene ether glycol is formed. Such product copolymers are "product polymers."

By "adding during the polycondensing of the reactants" is meant that base is administered repeatedly or continuously during the polycondensation reaction. It is desired that the acid catalyst in the reaction be titrated as the reaction progresses; thus, excluded is the addition of base in a single bolus or dose. In some embodiments, the base is administered continuously, and in some embodiments, the base is administered via multiple aliquots. The addition, regardless of method, need not occur over the entire length of the polymerization reaction. It is preferred that the addition occur over a sufficient period of the reaction to provide product polymer with improved color. Equipped with this disclosure, one of skill in the art will be readily able to determine the preferred period of addition to achieve desired results.

The processes disclosed herein are suitable for use in making polytrimethylene ether glycol having reduced color. Methods for making polytrimethylene ether glycol using an acid catalyst are disclosed in the art, for example, in U.S. Pat. Nos. 6,977,291 and 6,720,459.

It has been found that adding base over the course of the polycondensation reaction will reduce product polymer color, and that the reduction in color can be achieved without an unacceptable sacrifice in reaction time. Using the processes described herein, it is possible to achieve a desired reaction product with desired color properties.

It is also contemplated that use of the processes disclosed herein can provide efficiencies such as shortened polymerization time. Polymerization time can be decreased with the use of higher catalyst concentrations or increased reaction temperatures. The addition of base over the course of the polycondensation can be used to offset such aggressive reaction conditions chosen to shorten the polymerization time while ensuring acceptable product color.

The processes disclosed herein can be used for decolorization during preparation of polymers synthesized by polycondensation of 1,3-propanediol prepared from petrochemical sources, such as the process using acrolein, and for polymers prepared by polycondensation of 1,3-propanediol prepared by biochemical routes.

When the polycondensation reaction is carried out in the presence of a comonomer diol, at least one copolymer of polytrimethylene ether glycol is formed. In one aspect, the at least one comonomer diol is selected from the group consisting of 1,2-ethanediol, 2-methyl-1,3-propanediol, 2,2'-dimethyl-1,3-propanediol, 1-6-hexanediol, 1,7-heptanediol, 1,7-octanediol, 1,10-decanediol, and 1,12-dodecanediol. In a more specific aspect, the comonomer diol is 1,2-ethanediol. The reaction mixture can comprise up to about 30%, up to about 40%, or up to about 50% of comonomer diol by weight, based on the total weight of the reaction mixture.

In one embodiment the process can be carried out using at least one reactant selected from the group consisting of 1,3-propanediol, poly-1,3-propanediol (including, for example, dimers or trimers of 1,3-propanediol) and mixtures thereof, and at least one comonomer diol selected from the group consisting of ethanediol, C4 through C12 straight-chain diols, and C3 through C12 branched diols. In a more specific embodiment, the process of the invention can be carried out using at least one reactant selected from the group consisting of 1,3-propanediol, poly-1,3-propanediol (including, but not limited to, for example, dimers or trimers of 1,3-propanediol) and mixtures thereof, and at least one comonomer diol selected from the group consisting of 1,2-ethanediol, 2-methyl-1,3-propanediol, 2,2'-dimethyl-1,3-propanediol, 1-6-hexanediol, 1,7-heptanediol, 1,7-octanediol, 1,10-decanediol, and 1,12-dodecanediol.

Thermal stabilizers, antioxidants such as butylated hydroxyl toluene, and coloring materials can also be added to the reaction mixture or to the final polymer if desired.

In some embodiments, the polycondensation reaction is carried out under an inert atmosphere, such as nitrogen or argon. In other embodiments, the polycondensation reaction is carried out at a pressure of less than one atmosphere; in other embodiments the reaction is carried out at a pressure of less than 50 kPa or less than 25 kPa.

The polycondensation catalyst can be an inorganic or organic acid catalyst, and suitable polycondensation catalysts include both homogeneous and heterogeneous catalysts. Suitable polycondensation catalysts are described in the art (see, for example, U.S. Application Publication 2009/0118465).

The acid catalyst can be selected from the group consisting of Lewis acids, Bronsted acids, super acids, and mixtures thereof. In some embodiments, the suitable polycondensation catalyst is selected from the group consisting of inorganic acids, organic sulfonic acids including fluoroalkylsulfonic acids, heteropolyacids and metal salts.

In other embodiments, the catalyst is a homogeneous catalyst selected from the group consisting of sulfuric acid, hydroiodic acid, hydrochloric acid, hydrobromic acid, fluorosulfonic acid, phosphorous acid, p-toluenesulfonic acid, benzenesulfonic acid, methanesulfonic acid, phosphotungstic acid, nonafluorobutanesulfonic acid, trifluoromethanesulfonic acid, phosphomolybdic acid, 1,1,2,2-tetrafluoroethanesulfonic acid, 1,1,1,2,3,3-hexafluoropropanesulfonic acid, bismuth triflate, yttrium triflate, ytterbium triflate, neodymium triflate, lanthanum triflate, scandium triflate, and zirconium triflate. Homogeneous catalysts can also include rare earth acids of the form La(1,1,2,2,-tetrafluoroethane sulfonate)$_3$, La(1,1,2,3,3,3-hexafluoropropanesulfonates)$_3$, Sc(1,1,2,2,-tetrafluoroethane sulfonate)$_3$, Sc(1,1,2,3,3,3-hexafluoropropanesulfonates)$_3$, Ac(1,1,2,2,-tetrafluoroethane sulfonate)$_3$, Ac(1,1,2,3,3,3-hexafluoropropanesulfonates)$_3$, Yb(1,1,2,2,-tetrafluoroethane sulfonate)$_3$ and Yb(1,1,2,3,3,3-hexafluoropropanesulfonates)$_3$, as well as SbF$_5$—HF (magic acid) and mixtures of fluorosulfuric acid and antimony pentachloride, as described by G. A. Olah, G. K. Surya Prakash and J. Sommer in "Superacids" (John Wiley & Sons, NY, 1985).

The polycondensation catalyst can also comprise a heterogeneous catalyst selected from the group consisting of zeolites, fluorinated alumina, acid-treated alumina, heteropolyacids and heteropolyacids supported on zirconia, titania, alumina and/or silica, as well as ion exchange-based solid acid catalysts such as Amberlyst® 15 or perfluorinated ion exchange polymers.

In one aspect, the polycondensation catalyst is selected from the group consisting of trifluoromethanesulfonic acid, nonafluorobutanesulfonic acid, 1,1,2,2-tetrafluoroethanesulfonic acid, 1,1,2,3,3,3-hexafluoropropanesulfonic acid, sulfuric acid and perfluorinated ion-exchange polymers. Preferred acid catalysts include trifluoromethanesulfonic acid, 1,1,2,2-tetrafluoroethanesulfonic acid, and sulfuric acid. In a preferred embodiment, the polycondensation catalyst is sulfuric acid.

The amount of acid catalyst present at the beginning of the condensation reaction (referred to herein as the "initial amount of acid catalyst") is chosen based on factors such as desired reaction rate, desired product molecular weight, or in consideration of the particular catalyst. In some embodiments, the initial amount of acid catalyst is from about 0.01 weight percent to about 5 weight percent relative to the weight of the initial reaction mixture. In one embodiment, the initial amount of acid catalyst is from about 0.02 weight percent to about 1 weight percent. In still another aspect, the initial amount of acid catalyst is from about 0.03 weight percent to about 0.5 weight percent. In some embodiments, the catalyst is sulfuric acid and is present at about 0.1 weight percent to about 5 weight percent at the beginning of the polycondensation reaction. In some embodiments, the acid catalyst comprises sulfuric acid and is present at about 3 weight percent to about 5 weight percent at the beginning of the reaction. In some embodiments, the sulfuric acid catalyst is present at about 3 weight percent at the beginning of the reaction.

In one embodiment, the polycondensation reaction is carried out at a temperature of about 120° C. to about 250° C. In another embodiment, the polycondensation reaction is carried out at a temperature of about 120° C. to about 210° C. In yet another embodiment the polycondensation reaction is carried out at a temperature of about 140° C. to about 190° C. In yet another embodiment, the polycondensation reaction is carried out at a temperature of about 160° C. to about 180° C.

The time for the reaction to form the polymer is determined by factors such as the concentration of reactants, reaction conditions, reactor type, and operating conditions. A skilled artisan, equipped with this disclosure, will be readily able to adjust the time for the reaction to achieve desired yields of a reaction product having a desired molecular weight.

In some embodiments, base, preferably an aqueous basic solution, is added over the course of the polycondensation reaction in an amount sufficient to improve color of the product polymer without dramatically increasing the reaction time. The reaction time will preferably be in the range of about 3 to about 30 hours. Preferred reaction times are about 3 hours to about 24 hours or about 3 hours to about 12 hours. In some embodiments, the reaction time is about 6 to about 12 hours.

In some embodiments, base is added over the course of the polycondensation reaction in an amount not to exceed a concentration of base that causes the reaction time to increase by more than about 10%, more than about 30%, more than about 50%, more than about 70%, or more than about 100% as compared to the rate under the same polymerization conditions but without addition of base.

The base can be any base capable of neutralizing the acid catalyst, preferably not adversely affecting product quality. The base can be organic or inorganic. Preferred bases include sodium carbonate and sodium hydroxide, with sodium carbonate being most preferred.

The total amount of base to be added during the course of the polymerization is selected based on the desired adjustment of acid catalyst concentration. The acid catalyst at the end of the polycondensation is typically less than the amount present at the beginning of the polycondensation. One of skill in the art will appreciate how to calculate the reduction using the mass of base salt and adjusting for the stoichiometry of the acid-base titration. Typically, the total amount of base added is in an amount less than about 100% of the acid catalyst on a mole basis. In some embodiments, the total amount of base at the end of the reaction is about 5-10% of catalyst on a mole basis.

It is preferred that the base is added as an aqueous solution. Preferred aqueous solutions of base are about 0.1 to 10 wt %. It is preferred that the addition is continuous over a period of the polycondensation reaction, thus titrating the reaction mixture over the course of the reaction to reduce the acid catalyst concentration as the polymerization progresses. The basic solution is added continuously at a rate sufficient for color control while maintaining suitable polymerization rate. The rate of addition of the basic solution can be adjusted depending on the concentration of base in the solution, the amount of acid catalyst in the reaction, and the length of time over which the solution is to be added. In one embodiment, aqueous base solution is added in an amount of about 0.005 g/g to 0.03 g/g of reaction mixture. The base can be added continuously using equipment and methods known in the art. For example, a metering pump can be used to add aqueous solution continuously.

For the processes disclosed herein, it is preferred that there is at least one period of continuous addition of base during the polymerization reaction; in some embodiments, there are multiple periods of continuous addition during a given polymerization. For example, base can be added during multiple periods of the polymerization either intermittently or at regular intervals. Specifically excluded is the addition of base in a single bolus.

While base can be added during any period of the polymerization process, it is preferred that the addition is started prior to substantial color development, and preferably prior to color development to greater than about 250 APHA, more preferable prior to color development to greater than about 100 APHA, and even more preferably prior to color development to greater than about 50 APHA. In one embodiment, the addition occurs over the period of the reaction where molecular weight of about 200 is achieved until the desired molecular weight is achieved. In one embodiment, the addition is started concurrently with the start of the polymerization. In a preferred embodiment, the addition is started when the polymer has reached a molecular weight of about 200 to about 500.

In another embodiment, base is added in multiple aliquots over the course of the polycondensation. In one embodiment, the first aliquot of base is introduced into the reaction mixture concurrently with the start of the polymerization. In another embodiment, the first aliquot is added to the reaction mixture when the polymer has reached a molecular weight of about 200 to about 500. The desired frequency of addition and the concentration of the aliquots depends on the desired product polymer color. For a given reaction, individual aliquots can be of the same concentration, or may be of varied concentration.

The molecular weight of the product polymer or copolymer is preferably about 500 to about 5000. In some embodiments, the molecular weight of the product polymer or copolymer is at least about 1000. In some embodiments, the molecular weight of the product polymer or copolymer is at least about 1400.

APHA color values are a measure of color as defined in ASTM-D-1209 (see Test Method 1, below). Preferred color values can vary depending on the desired molecular weight and/or the desired end use of the product. However, armed with this disclosure, one of skill in the art will be able to readily adjust the process conditions to achieve the desired effect on the color of the product. The processes described herein will preferably result in polymer with an APHA color of less than about 250, preferably less than about 100, and, more preferably, less than 50. The APHA color can be less than about 40 or less than about 30. In certain embodiments, the APHA color is about 30 to about 100 APHA.

The processes disclosed herein can be used in conjunction with methods wherein the raw materials are pretreated to remove color (such as, for example, in U.S. Pat. No. 6,235,948), or methods wherein the polymer products are post-treated to remove color (such as, for example, in U.S. Pat. No. 7,294,746). In some embodiments, the processes disclosed herein can eliminate or diminish the necessity of pre- or post-treatment steps and still produce polymer of desirable APHA color. Thus, another embodiment of the present invention is a process consisting of polycondensing reactants comprising 1,3-propanediol, poly-1,3-propanediol, or mixtures thereof in the presence of an acid catalyst and adding base during the polycondensing of the reactants.

Other post-polymerization purification procedures are known, and can be used in conjunction with the processes disclosed herein. For example, U.S. Pat. No. 7,388,115 discloses a process of removing acid esters formed from reaction of the catalyst with the hydroxyl compounds by adding water to the polymer in a hydrolysis step prior to addition of water-soluble inorganic compounds and further purification steps.

U.S. Pat. Nos. 7,161,045 and 7,157,607 disclose processes for preparing polytrimethylene ether glycol wherein the phase separation after hydrolysis is promoted by addition of organic solvent.

EXAMPLES

Materials, Equipment and Test Methods
Materials:
For Examples 1-5, the 1,3-propanediol monomer used was bio-derived and is commercially available from DuPont Tate & Lyle Bio-Products LLC.
Test Method 1: Color Measurement and Apha Values
A Hunterlab Color Quest XE Spectrocolorimeter (Reston, Va.) was used to measure the polymer color. Color numbers of the product polymer are measured as APHA values (Platinum-Cobalt System) according to ASTM D-1209. The polymer molecular weights were calculated from their hydroxyl numbers obtained from NMR Comparative Example A Control Experiment In a 20 L glass reactor equipped with a condenser and an agitator, 8 kg of 1,3-propanediol monomer was added, then purged with $N_2$ at a rate of 5 L/min. The reactant was heated up to 160° C. with an agitation speed of 250 rpm. When the reactant mixture temperature reached 160° C., 250 g of sulfuric acid was added to the reactor. The time for sulfuric acid addition was set as the reaction starting point. Polymerization proceeded at 160° C. The reaction volatiles were condensed in the condenser and polymer product was accumulated in the reactor. Polymer samples were taken periodically for color and molecular weight analysis. The polymer molecular weights were determined from NMR integrations of the protons adjacent to terminal hydroxyl groups and polymer ether links. The ratio of these two integrations provides the hydroxyl number and number average molecular weight of the polymer. The product color was determined using a Hunter Lab Color quest XE machine and expressed as APHA index. The results are shown in Table A.

TABLE A

Results of Comparative Example A

| Reaction Time (hr) | Mn | Color (APHA) |
|---|---|---|
| 5 | 655 | 50 |
| 6 | 882 | 124 |
| 7 | 1123 | 360 |
| 8 | 1301 | 500 |
| 9 | 1592 | >500 |

Example 1

The equipment and polymerization procedures were the same as in Comparative Example A, except that an aqueous solution of sodium carbonate was added continuously to the reactor. $Na_2CO_3$ was dissolved in deionized water prior to the experiment to form an aqueous solution of 7.5 wt %. When the polymerization had reached a molecular weight of 287, the aqueous solution of $Na_2CO_3$ was added to the reactor continuously at a rate of 1.5 g/min. Polymer samples were taken for molecular weight ($M_n$) and color analysis. The results are shown in Table 1 and FIG. 1.

TABLE 1

Results of Example 1

| Reaction Time (hr) | Mn | Color (APHA) |
|---|---|---|
| 4.25 | 334 | 38 |
| 6.25 | 538 | 40 |
| 8.25 | 1346 | 45 |
| 11.25 | 1616 | 65 |

Example 2

The equipment and polymerization procedures were the same as in Comparative Example A, except that 12 kg of 1,3-propanediol and 375 g of sulfuric acid were used and an aqueous solution of sodium hydroxide was added continuously to the reactor over a period of the polycondensation reaction. NaOH was dissolved in deionized water prior to the experiment to form an aqueous solution of 2.5 weight percent. When the polymerization had reached an $M_n$ of 246, the aqueous solution of NaOH was added to the reactor continuously at a rate of 2.3 g/min. Polymer samples were taken for $M_n$ and color analysis. The results are shown in Table 2.

TABLE 2

Results of Example 2

| Reaction Time (hr) | Mn | Color (APHA) |
|---|---|---|
| 5.5 | 566 | 38 |
| 7.0 | 881 | 50 |
| 8.5 | 1091 | 131 |
| 11.8 | 1527 | 190 |

Comparative Example B

Control Experiment

In a 1 L glass Morton reactor equipped with a condenser and an agitator, 800 g of 1,3-propanediol monomer and 25 g of sulfuric acid were combined and purged with $N_2$ at a rate of 0.5 L/min. The reactant mixture was heated to 180° C. with an agitation speed of 350 rpm. The time at which the heating started was set as the reaction starting point. The reactant mixture reached temperature within 1.25 hr and polymerization proceeded at 180° C. The reaction volatiles were condensed in the condenser and polymer product was accumulated in the reactor. Polymer samples were taken periodically for color and molecular weight analysis. The number average molecular weight of polymer was determined by the NMR method and the product color was determined using a LaMotte SMART 2 colorimeter calibrated to a 500 APHA Platinum-Cobalt standard. Polymer samples were compared to deionized water samples in 25 mm diameter sample cells. The results are shown in Table B and expressed as APHA index.

TABLE B

Results of Comparative Example B

| Reaction time (hr) | Mn | Color (APHA) |
|---|---|---|
| 1.25 | 200 | <30 |
| 2.33 | 752 | <30 |

TABLE B-continued

Results of Comparative Example B

| Reaction time (hr) | Mn | Color (APHA) |
|---|---|---|
| 3.25 | 1200 | 124 |
| 4.33 | 1429 | 529 |

Example 3

The equipment and polymerization procedures were the same as in Comparative Example B, except that an aqueous solution of sodium carbonate was added continuously to the reactor from the beginning of reactor heating at a rate of 0.15 g/min. $Na_2CO_3$ was dissolved in deionized water prior to the experiment to form an aqueous solution of 2 weight percent. The time at which the heating started was set as the reaction starting point. The reactant mixture reached temperature within 1.28 hr and polymerization proceeded at 180° C. Polymer samples were taken for $M_n$ and color analysis. The results are shown in Table 3.

TABLE 3

Results of Example 3

| Reaction Time (hr) | Mn | Color (APHA) |
|---|---|---|
| 1.28 | 228 | <30 |
| 2.70 | 1031 | <30 |
| 3.28 | 1225 | <30 |
| 4.28 | 1349 | 52 |
| 5.28 | 1388 | 121 |
| 6.28 | 1430 | 231 |

Comparative Example C

Control Experiment

In a 20 L glass reactor equipped with a condenser and an agitator, 12 kg of 1,3-propanediol monomer was added and purged with $N_2$ at a rate of 5 L/min. The reactant mixture was heated to 170° C. with an agitation speed of 250 rpm. When the reactant mixture temperature reached 170° C., 187.5 g of sulfuric acid was added to the reactor. The time for sulfuric acid addition was set as the reaction starting point. Polymerization proceeded at 170° C. The reaction volatiles were condensed in the condenser and polymer product was accumulated in the reactor. Polymer samples were taken periodically for color and molecular weight analysis. The number average molecular weight of polymer was determined by the NMR method and the product color was determined using a Hunter Lab Color quest XE machine and expressed as APHA index. The results are shown in Table C.

TABLE C

Results of Comparative Example C

| Reaction Time (hr) | Mn | Color (APHA) |
|---|---|---|
| 3 | 226 | 18 |
| 4 | 326 | 26 |
| 5 | 496 | 44 |
| 6 | 662 | 70 |
| 7 | 824 | 99 |

TABLE C-continued

Results of Comparative Example C

| Reaction Time (hr) | Mn | Color (APHA) |
|---|---|---|
| 12 | 1592 | 397 |
| 14 | 2000 | >500 |

Example 4

Figure 2:
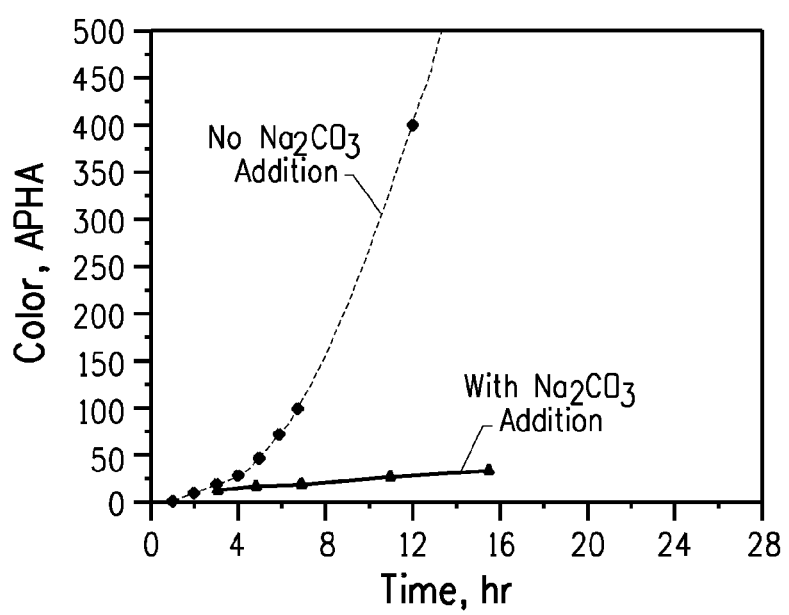
FIG. 2 illustrates the effect of continuous addition of sodium carbonate aqueous solution on polytrimethylene ether glycol color development; 170° C., 1.5 wt % of sulfuric acid.
Figure 3:
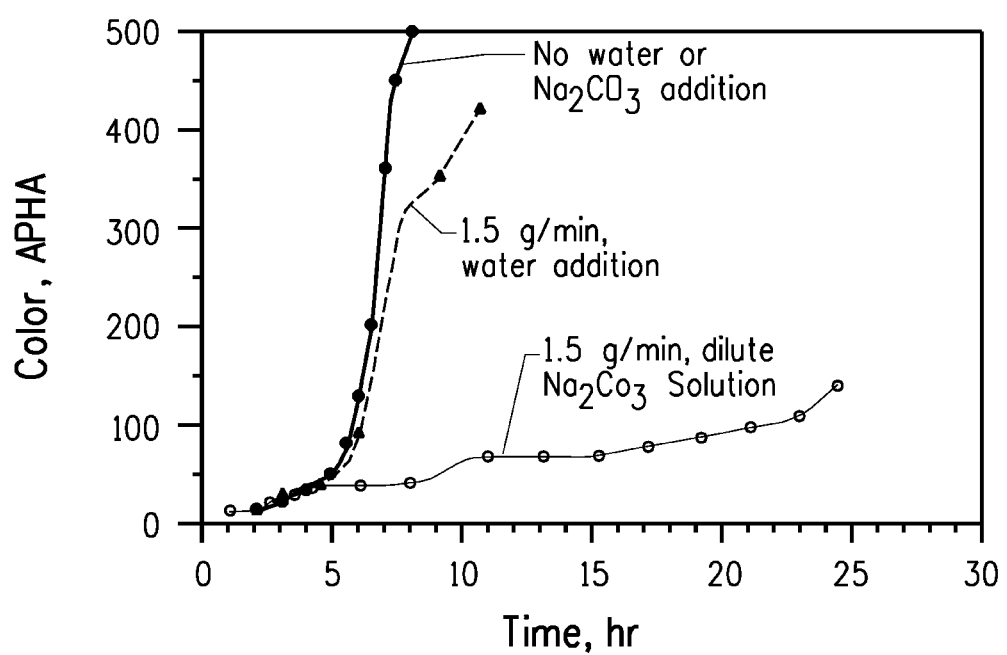
FIG. 3 illustrates the effect of continuous addition of sodium carbonate aqueous solution (7.5 wt %) or water on product color.

The equipment and polymerization procedures were the same as in Comparative Example C, except that an aqueous solution of sodium carbonate was added continuously to the reactor at an $M_n$ of 230 (3 hr of reaction time). $Na_2CO_3$ was dissolved in deionized water prior to the experiment to form an aqueous solution of 0.5 wt %. When the polymerization reached an $M_n$ of 230, the aqueous solution of $Na_2CO_3$ was added to the reactor continuously at a rate of 4.0 g/min. Polymer samples were taken for $M_n$ and color analysis. The results are shown in Table 4 and FIG. 2.

TABLE 4

Results of Example 4

| Reaction Time (hr) | Mn | Color (APHA) |
|---|---|---|
| 3 | 236 | 11 |
| 5 | 386 | 15 |
| 7 | 668 | 18 |
| 11 | 1193 | 28 |
| 15.5 | 1628 | 34 |

Example 5

The equipment and polymerization procedures were the same as in Comparative Example C, except that an aqueous solution of $Na_2CO_3$ was added continuously to the reactor at an $M_n$ of 230 (3 hr of reaction time). $Na_2CO_3$ was dissolved in deionized water prior to the experiment to form an aqueous solution of 1.0 wt %. When the polymerization had reached an $M_n$ of 230, the aqueous solution of $Na_2CO_3$ was added to the reactor continuously at a rate of 4.0 g/min. The polymer samples were taken for $M_n$ and color analysis. The results are shown in Table 5.

TABLE 5

Results of Example 5

| Reaction Time (hr) | Mn | Color (APHA) |
|---|---|---|
| 3 | 235 | 9 |
| 6 | 480 | 14 |
| 10.5 | 1027 | 21 |
| 13.5 | 1447 | 26 |

What is claimed is:
1. A process comprising
   a) polycondensing reactants comprising 1,3-propanediol, poly 1,3-propanediol, or mixtures thereof and optionally a comonomer diol in the presence of an acid catalyst to form a product polymer; and
   b) adding an inorganic base continuously during the polycondensing of the reactants, wherein the total amount of base added is in an amount less than about 100% of the acid catalyst on mole basis, and wherein the adding of base is started when the polymer product has reached a molecular weight of about 200.

2. The process of claim 1 wherein the base is added in multiple aliquots.

3. The process of claim 1 wherein the total amount of base added is greater than about 5% and less than about 100% of the acid catalyst on a mole basis.

4. The process of claim 1 wherein the acid catalyst is trifluoromethanesulfonic acid, 1,1,2,2-tetrafluoroethanesulfonic acid, or sulfuric acid.

5. The process of claim 1 wherein the catalyst is sulfuric acid and is present prior to the adding of base and is in an amount of about 0.1 weight percent to about 5 weight percent based on the total weight of the reactants.

6. The process of claim 1 wherein the base is sodium carbonate or sodium hydroxide.

7. The process of claim 1 wherein the optional comonomer diol is 1,2-ethanediol.

8. The process of claim 1 wherein the product polymer is polytrimethylene ether glycol.

\* \* \* \* \*